United States Patent
Zanos et al.

(10) Patent No.: US 11,872,371 B2
(45) Date of Patent: Jan. 16, 2024

(54) SYSTEMS AND METHODS FOR REAL-TIME MONITORING OF PHYSIOLOGICAL BIOMARKERS THROUGH NERVE SIGNALS AND USES THEREOF

(71) Applicant: THE FEINSTEIN INSTITUTES FOR MEDICAL RESEARCH, Manhasset, NY (US)

(72) Inventors: Theodoros Zanos, Astoria, NY (US); Todd Levy, Kew Gardens, NY (US); Emily Battinelli, Franklin Square, NY (US); Kevin J. Tracey, Old Greenwich, CT (US); Chad E. Bouton, Darien, CT (US); Sangeeta Chavan, Syosset, NY (US); Harold Silverman, Plainview, NY (US)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 708 days.

(21) Appl. No.: 16/605,818

(22) PCT Filed: Apr. 19, 2018

(86) PCT No.: PCT/US2018/028243
§ 371 (c)(1),
(2) Date: Oct. 17, 2019

(87) PCT Pub. No.: WO2018/195238
PCT Pub. Date: Oct. 25, 2018

(65) Prior Publication Data
US 2020/0179600 A1  Jun. 11, 2020

Related U.S. Application Data

(60) Provisional application No. 62/487,865, filed on Apr. 20, 2017.

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *A61B 5/14546* (2013.01);
(Continued)

(58) Field of Classification Search
CPC .. A61N 1/36053; A61N 1/36139; A61N 7/00; A61N 2007/0026; A61B 5/6877;
(Continued)

(56) References Cited

U.S. PATENT DOCUMENTS 7,167,751 B1 * 1/2007 Whitehurst .......... A61N 1/3605
607/40
7,988,630 B1 8/2011 Osorio et al.
(Continued)

FOREIGN PATENT DOCUMENTS

| WO | 2016134197 A1 | 8/2016 |
| WO | 2016134199 A1 | 8/2016 |
| WO | 2016141184 A1 | 9/2016 |

OTHER PUBLICATIONS

Ngkelo et al.; LPS induced inflammatory responses in human peripheral blood mononuclear cells is mediated through NOX4 and Giα dependent PI-3kinase signalling; published on Jan. 12, 2012; Journal of Inflammation; 9, Article No. 1 (2012) (Year: 2012).*
(Continued)

*Primary Examiner* — Chao Sheng
(74) *Attorney, Agent, or Firm* — Amster, Rothstein & Ebenstein LLP

(57) ABSTRACT

The present disclosure relates to systems, methods and devices to monitor, diagnose and/or treat diseases or disorders comprising a calibration phase and a real-time diag-
(Continued)

nostic, treatment or monitoring phase, the calibration phase correlating a plurality of nerve activity measurements from a chronically implanted electrode in a subject with a plurality of concurrent measurements of levels of cytokines and/or glucose in the blood to obtain a functional relationship between blood cytokine and/or glucose levels and vagus nerve activity, and the diagnostic, treatment or monitoring phase analyzing the subject's real-time vagus nerve activity in accordance with the previously obtained functional relationship to initiate a treatment method.

13 Claims, 12 Drawing Sheets

(51) Int. Cl.
*A61B 5/00* (2006.01)
*A61N 1/36* (2006.01)
*A61N 7/00* (2006.01)
*A61B 5/388* (2021.01)

(52) U.S. Cl.
CPC ............ *A61B 5/388* (2021.01); *A61B 5/7225* (2013.01); *A61B 5/7264* (2013.01); *A61B 5/7282* (2013.01); *A61N 1/36053* (2013.01); *A61N 1/36139* (2013.01); *A61N 7/00* (2013.01); *A61B 2560/0214* (2013.01); *A61B 2560/0238* (2013.01); *A61N 2007/0026* (2013.01)

(58) Field of Classification Search
CPC ......... A61B 5/14532; A61B 5/40; A61B 5/24; A61B 5/388; A61B 5/14546; A61B 5/7225; A61B 5/7264; A61B 5/7782; A61B 2560/0214; A61B 2560/0238
See application file for complete search history.

(56) References Cited

U.S. PATENT DOCUMENTS

| | | | |
|---|---|---|---|
| 9,662,490 | B2 | 5/2017 | Tracey et al. |
| 10,166,395 | B2 | 1/2019 | Tracey et al. |
| 2006/0259077 | A1* | 11/2006 | Pardo ................. A61N 1/36053 607/40 |
| 2008/0312714 | A1 | 12/2008 | Pasricha et al. |
| 2009/0254143 | A1 | 10/2009 | Tweden et al. |
| 2010/0145222 | A1* | 6/2010 | Brunnett ................. A61B 5/05 600/554 |
| 2010/0280562 | A1 | 11/2010 | Pi et al. |
| 2011/0066209 | A1* | 3/2011 | Bodlaender ........ A61N 1/36021 607/46 |
| 2013/0060296 | A1* | 3/2013 | Wenzel ................... A61B 5/24 607/18 |
| 2014/0279746 | A1 | 9/2014 | De Bruin et al. |
| 2015/0216483 | A1 | 8/2015 | Sevcencu et al. |
| 2016/0067497 | A1* | 3/2016 | Levine ................. A61B 5/4836 607/62 |
| 2016/0250097 | A9 | 9/2016 | Tracey et al. |
| 2016/0256683 | A1* | 9/2016 | Butera ............... A61N 1/36053 |
| 2018/0021214 | A1 | 1/2018 | Tracey et al. |
| 2018/0021580 | A1 | 1/2018 | Tracey et al. |
| 2019/0247659 | A1 | 8/2019 | Kressel et al. |
| 2019/0255175 | A1 | 8/2019 | Tracey et al. |

OTHER PUBLICATIONS

Niijima; Neural Control of Blood Glucose Level; published in 1986; The Japanese Journal of Physiology; 1986 vol. 36 Issue 5 pp. 827-841 (Year: 1986).*
PCT International Search Report and Written Opinion dated Jul. 9, 2018 in connection with PCT International Application No. PCT/US2018/028243, 12 pages.
Extended European Search Report dated Nov. 30, 2020 from European Patent Appln. No. 18788381.4.

* cited by examiner

Fig. 2A                     Fig. 2B

SYSTEMS AND METHODS FOR REAL-TIME MONITORING OF PHYSIOLOGICAL BIOMARKERS THROUGH NERVE SIGNALS AND USES THEREOF

STATEMENT OF GOVERNMENT SUPPORT

This invention was made with government support under grant numbers W911NF-09-1-0125 and HR0011-15-2-0016 awarded by the Defense Advanced Research Projects Agency (DARPA). The government has certain rights in the invention.

CROSS-REFERENCE TO RELATED APPLICATIONS

This application is a U.S. national stage entry under 35 U.S.C. § 371 of PCT International Patent Application No. PCT/US2018/028243, filed Apr. 19, 2018, which claims the benefit of U.S. Provisional Patent Application No. 62/487,865, filed Apr. 20, 2017, the contents of which are incorporated herein by reference into the subject application.

TECHNICAL FIELD

The present disclosure relates to systems, devices and methods that process neural signals of a mammal, particularly a human.

BACKGROUND

The central nervous system (CNS) is a complex system in a mammal. Chemical, mechanical, and electromagnetic signals are sensed by neurons, which propagate action potentials to the CNS. These comprise the afferent arcs of reflex circuits that maintain the body's homeostasis. This fundamental principle of sensing environmental and internal changes in order to mount appropriate reflex responses is central to the physiological mechanisms that allow for not only homeostasis but adaptability and species survival.

The armaments of treatment options available to a physician to treat conditions, disorders or diseases have increased tremendously, especially in the last century. However, while the number of treatment options has increased, treatment protocols directed at the underlying cause of a condition are more limited. For example, millions of patients suffer from glucose-level disorders resulting from pancreas-related disorders. Pancreas-related disorders are often treated using drugs and/or biological compounds, such as hormones, artificial insulin, etc. However, drugs and biologics cause insulin resistance against these disorders. Additionally, hormone therapy may cause various undesirable side effects.

Products of the immune system, including cytokines and other mediators, are sensed by the nervous system, such that the immune system can serve as a functional sensory modality. In this context, foreign invaders, microbial products, and other exogenous immune stimulators culminate in the release of cytokines. These immune products can in turn interact with the peripheral nervous system and the CNS to elicit neurophysiological responses.

There continues to be an interest in the development of new protocols, systems, devices and treatment options for treating various conditions. Particularly, protocols for treating conditions directed at the cause of the conditions continue to be a center of scientific innovation and interest. In bioelectronic medicine and neuroscience, one of the biggest challenges is the ability to record, extract and identify information from nerves. It is highly desirable to measure activities in nerves both, for diagnostic purpose and as treatment options. However, in the past, interferences, for example, such as cardio-electric or respiratory interference, presented a major problem. Further, correlating information obtained from nerve and brain activity to a human bodily function to effect diagnosis, treatment and/or monitoring of disease condition has been limited.

The present invention addresses the need for improved methods for treating diseases and disorders, in particular methods that are based on real-time physiological measurements from the patient that is being treated, and thus provide personalized medicine.

SUMMARY

The present application discloses systems, devices and methods for the diagnosis, treatment and monitoring of symptoms of diseases or disorders based on the information exchange and nerve activity between the different organs of the human body and the brain.

The invention provides a method for diagnosing or treating or monitoring symptoms in a subject with diabetes based on the subject's vagus nerve activity, comprising a calibration phase and a real-time diagnostic, treatment or monitoring phase, wherein the calibration phase precedes the diagnostic, treatment or monitoring phase, and wherein the calibration phase comprises correlating a plurality of vagus nerve activity measurements from a chronically implanted electrode in the subject with a plurality of concurrent measurements of glucose levels in the blood of the subject to obtain a functional relationship between blood glucose levels and vagus nerve activity recorded from the implanted electrode in the subject; and the diagnostic, treatment or monitoring phase comprises analyzing the subject's real-time vagus nerve activity in accordance with the previously obtained functional relationship to initiate a treatment method.

The invention also provides a method for diagnosing or treating or monitoring symptoms in a subject with a cytokine-mediated disease or disorder based on the subject's vagus nerve activity, comprising a calibration phase and a real-time diagnostic, treatment or monitoring phase, wherein the calibration phase precedes the diagnostic, treatment or monitoring phase, and wherein the calibration phase comprises correlating a plurality of vagus nerve activity measurements from a chronically implanted electrode in the subject with a plurality of concurrent measurements of levels of one or more cytokines in the blood of the subject to obtain a functional relationship between blood cytokine levels and vagus nerve activity recorded from the implanted electrode in the subject; and the diagnostic, treatment or monitoring phase comprises analyzing the subject's real-time vagus nerve activity in accordance with the previously obtained functional relationship to initiate a treatment method.

The invention further provides an implantable system for monitoring, diagnosing and/or treating a disease or disorder in a subject, wherein the system comprises one or more pairs of electrodes for recording nerve activity from the subject, an interface to capture the nerve activity, a digitizer to digitize the nerve activity, a processor for processing the digitized nerve activity, a wireless external device interface for inputting biological signals to the processor and for outputting signals from the processor, and a rechargeable or replaceable battery; wherein the system is configured to perform a method comprising a calibration phase and a real-time diagnostic, treatment or monitoring phase, wherein the calibration phase precedes the diagnostic, treatment or monitoring phase, and wherein the calibration phase comprises correlating a plurality of nerve activity measurements from a chronically implanted electrode in a subject with a plurality of concurrent measurements of levels of one or more cytokines and/or glucose in the blood of the subject to obtain a functional relationship between blood cytokine levels and/or blood glucose levels and vagus nerve activity recorded from the implanted electrode in the subject; and the diagnostic, treatment or monitoring phase comprises analyzing the subject's real-time vagus nerve activity in accordance with the previously obtained functional relationship to initiate a treatment method.

BRIEF DESCRIPTION OF THE DRAWINGS

FIG. 2A-2E. Preprocessing framework. (A) The raw recorded signal, (B) wavelet decomposition, (C) adaptive thresholding, (D) dimensionality reduction through t-SNE, clustering using the DBSCAN method, and splitting clusters based on their range of amplitudes, and (E) resulting CAP waveforms and Inter-CAP Interval Histograms.

DETAILED DESCRIPTION

Figure 1A:
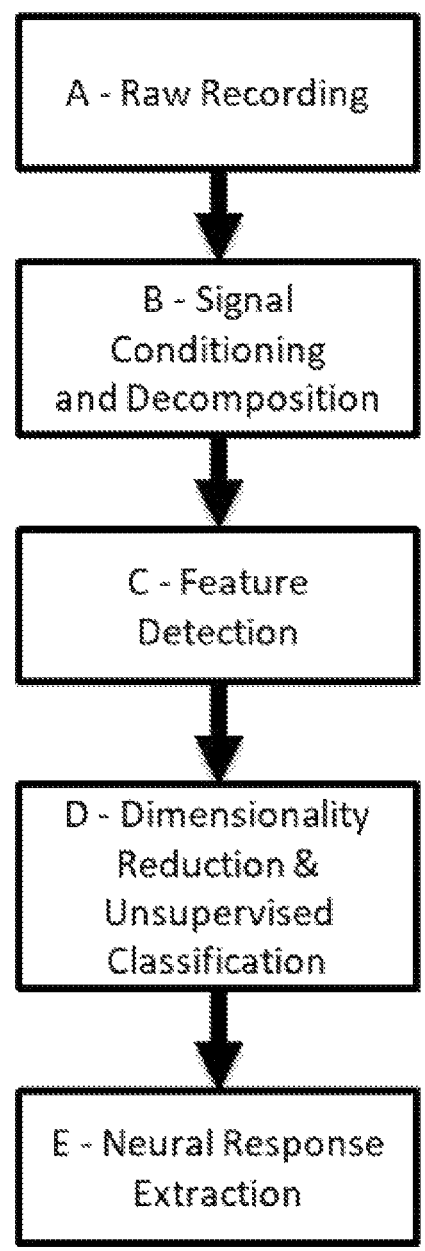
FIG. 1A-1C. Nerve recording processing methodological framework (A) Schematic diagram of the preprocessing data analysis methodological framework with all the steps carried out to extract neural responses/event rates. (B) Schematic Diagram of the decoder used to discriminate between no injection (baseline), IL-1β or TNF injection. (C) Schematic Diagram of the decoder used to regress to blood glucose levels after insulin injection.

Illustrative embodiments of the disclosure are described herein. Certain terms are used throughout the following description and claims refer to particular system components. Components may be referred to by different names. This document does not intend to distinguish between components that differ in name but not function.

Definitions

To facilitate an understanding of the present disclosure, a number of terms and phrases are defined below. As used herein, the term "subject" refers to a mammal or other vertebrate animal, preferably a human. It is intended that the term encompass human patients and veterinary patients. Specific examples of a "patient" include, but are not limited to: individuals requiring medical assistance, individuals not requiring immediate medical attention, individuals monitoring one or more aspect of their health, individuals monitoring a disease condition, individual having a certain disease condition, healthy individuals, individuals with limited function, and individuals with lost motor or other function due to traumatic injury or neurological condition, disease or disorder.

The term "cellular signals," as used herein, refers to signals or combination of signals that may emanate from any living cell, such as, for example, subcellular signals, intracellular signals, and extracellular signals. For example, "cellular signals" may include, but not be limited to: neural signals (e.g., neuronal action potentials or spikes, local field potential (LFP) signals; glial cell signals; stomach cell signals; kidney cell signals; liver cell signals; pancreas cell signals; osteocyte cell signals; sensory organ cell signals (e.g., signals emanating from the eye or inner ear); tumor cell signals; and tooth cell signals. Signals may emanate from one or more cells, tissues, or organs or signals may be derived from part of a cell, tissue or organ. Signal may be extracellular or intracellular and may be generated at all atomic/cellular levels of the organ.

As used herein, the term "electrode" refers to a conductor used to establish electrical contact with a nonmetallic part of a circuit, in particular, part of a biological system (e.g., nerves and/or neural pathways). The term "housing" refers to the structure encasing or enclosing at least one component of the devices of the present disclosure.

As used herein, the term "implantable" refers to any device that may be implanted in a patient. It is intended that the term encompass various types of implants. In preferred embodiments, the device may be implanted under the skin (i.e., subcutaneous), or placed at any other location suited for the use of the device. An implanted device is one that has been implanted within a subject, while a device that is "external" to the subject is not implanted within the subject (i.e., the device is located externally to the subject's skin).

As used herein, the term "processor" refers to a device that is able to read a program or set of instructions from a computer memory (e.g., ROM or other computer memory) and perform or execute a set of steps according to the program or instructions. Processors may include non-algorithmic signal processing components (e.g., for analog signal processing) or algorithmic signal processing components.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape. As used herein, the term "computer readable medium" refers to any device or system for storing and providing information (e.g., data and instructions) to a computer processor. Examples of computer readable media include, but are not limited to, DVDs, CDs, hard disk drives, magnetic tape, flash memory, and servers for streaming media over networks.

The human body has built-in biological sensors that continuously monitor organ function and detect changes in the human body. Changes may relate to the cellular functioning, tissues or organs. Changes in the body are generally related to biomarkers and/or physiological parameters. The present application discloses a system, device and methods to leverage the vast network of nerve biosensors and/or physiological parameters to monitor, diagnose and/or treat various disease states, disorders and/or conditions, for example by recording neural signals emanating from and propagating through peripheral nerves, and using the neural signals and the pathways to diagnose, monitor and/or treat disease states, disorders and/or conditions.

As used herein, to "treat" a disease, disorder or condition means to alleviate or ameliorate or eliminate a sign or symptom of the disease, disorder or condition that is being treated.

Neural signals are acquired from surface nerve electrodes and represent an aggregate of the activity of multiple nerve fibers or fascicles. Neural signals are prone to various sources of noise, both physiological (cardiac, respiratory), and instrumentation. According to an embodiment of the present disclosure, the nerve activity is monitored, detected, isolated, decoded and correlated to one or more disease states, conditions and/or disorders. The correlation, for example, is related to the nerve activity or the neural signals emanating from biomarkers or other related physiological parameters, thereby resulting in diagnosis, real-time monitoring and/or treatment of disease state, condition and/or disorder.

Biomarkers include, but not limited to, glucose and cytokines. According to the present disclosure, a neural signal decoding algorithm can be trained to recognize the presence and/or estimate the level of one or more biomarkers using the methods and systems described herein. Included within the scope of the present disclosure are all known cytokines, which are incorporated herein by reference for all purposes, including, but not limited to, the following cytokines. Interleukin-1 beta (IL-1β) is one of the key mediators of the inflammatory response to physical stress. Higher levels are associated with anxiety, panic disorders, and cardiovascular risk. Interleukin-6 (IL-6)—Elevated IL-6 may occur in different conditions including chronic infections, autoimmune disorders, certain cancers and Alzheimer's disease. Interleukin-8 (IL-8)—Elevated blood levels of IL-8 are associated with rheumatoid arthritis, tumor development and Hepatitis C. Tumor necrosis factor alpha (TNF-α)—TNF-α is a growth factor for immune cells and osteoclasts, the cells that break down bone. It may be elevated in chronic infections, certain cancers and Hepatitis C.

Embodiments of the subject matter of the present disclosure provide a closed loop system for diagnosis, treatment and/or monitoring of one or more disease state, condition or disorders. Various embodiments include a combination of sensing nervous activity, decoding the sensed nervous activity, correlating the nerve activity to at least one physiological parameter, and/or related biomarker and/or stimulating nerve endings or the nervous pathways. Both efferent pathways and/or afferent pathways may be sensed and decoded. The correlation step is further related to the nerve activity or the neural signals emanating from the biomarker or other related physiological parameter, thereby resulting in diagnosis, real-time monitoring and/or treatment of the disease state, condition and/or disorder.

Nerve traffic comprises signals from cells, tissues, and/or one or more organs. The nerve traffic is sensed at nerves, for example, vagus nerve or any afferent nerve, such as carotid or aortic nerves. According to an embodiment of the present disclosure, the systems and methods are provided for monitoring, detecting and correlating nerve activity to disease, condition or disorders. The system and method further comprises autonomic modulation and delivery of nerve stimulation, thus providing a closed loop system that monitors neural activity continuously, in real time and provides correlation to the disease or disorder. Thus, it is also an objective of the present disclosure to provide a real-time monitoring and diagnosis system for the treatment of a disease or condition based on the neural activity of the human body.

As a non-limiting example, the disclosure provides method for diagnosing and/or treating a subject having inflammation, hypoglycemia or hyperglycemia. The method comprising sensing nerve activity emanating from and propagating through the cervical vagus nerve of the subject, monitoring nerve activity emanating from sensory neuronal circuits of at least one biomarker and/or related physiological parameter, decomposing nerve signals and correlating the decomposed nerve signals to a biomarker, thus decoding an endogenous mediator or pharmacologic agent related to inflammation, hypoglycemia or hyperglycemia. The method can also comprise electrically stimulating the cervical vagus nerve of the subject in an amount and manner effective to treat inflammation, hypoglycemia or hyperglycemia.

Changes in peripheral inflammatory and immune states are monitored from the nerve activity emanating from and to the cervical vagus nerve. Such nerve activity is decoded and correlated to a disease, disorder or condition or an endogenous mediator or pharmacologic agent. In an embodiment, delivery of nerve stimulation is performed to provide a closed loop system to continuously monitor neural activity in real time. In one specific embodiment, the method for treating the disease includes correlating the nerve activity to at least one biomarker and/physiological parameter, and comparing the correlated activity to a database that includes information regarding the physiological parameter in a normal state and the disease state.

In one specific embodiment, the present disclosure provides methods for monitoring and treating a subject having inflammation, or immune related disease. The method comprising monitoring nerve activity of the subject, decoding nerve signals and correlating the nerve signals to cytokine production, inflammatory receptors, mediators, or immune markers. The method further comprises delivery of nerve stimulation to provide a closed loop system and to continuously monitor neural activity in real-time and thereby, provide correlation to one or more disease or disorder.

Electrical signals move down the vagus nerve to the celiac ganglion from which the splenic nerve further propagates the signal towards the spleen. Within the spleen, a specialized subset of T lymphocytes completes the link between the nervous and immune systems. Acetylcholine released by the T cells down-regulates cytokine production by resident macrophage populations producing a systemic anti-inflammatory effect. Physiological status of cells and organs travel the vagus nerve from the periphery into the CNS. Such signals include the inflammatory status of the animal. For example, IL-1β might activate peripheral afferents of the vagus nerve that would signal to the central nervous system about the presence of the cytokine IL-1β. Similarly, TNF and IL-1β receptors are able to change activation thresholds when exposed to the corresponding exogenous cytokines.

The present disclosure provides methods to monitor nerve activity at the vagus nerve and decode nerve signals and correlate nerve signals to changes in peripheral inflammatory and immune states. Embodiment further provides methods to provide delivery of nerve stimulation to provide a closed loop system to continuously monitor neural activity in real time and thereby, provide correlation to the disease or disorder, continuously, in real-time.

Embodiments of the present disclosure provide methods for monitoring and treating a subject having metabolic disease or disorders associated with pancreas. Disorders include, without limiting, hypoglycemic conditions, hyperglycemic conditions, diabetic and/or pancreas related disorders.

The pancreas is a relatively small organ, approximately six inches long for an average person. The pancreas is positioned proximate the upper abdominal region, is connected to the small interior region, and is located in the posterior part of the body proximate the spine. The deep location of the pancreas renders diagnoses of disorders related to the pancreas difficult. The pancreas secretes enzymes that assist in digesting protein, fat, and carbohydrates before being absorbed by the body via the intestines. Additionally, the pancreas also generates regions of endorphin cells that produce insulin. Insulin regulates the use and storage of the body's main energy source, glucose. Thus, the pancreas has two vital roles in the body, which is an exocrine function and an endocrine function.

The pancreas houses a plurality of clusters of endocrine cells and a mass of exocrine tissue and associated ducts. The ducts produce an alkaline fluid containing digestive enzymes, which are delivered to the small intestine to assist in digestion and metabolism. Scattered throughout the exocrine tissue are various clusters of endocrine cells that produce insulin, glycogen, and various hormones. Insulin and glycogen serve as regulators of the blood glucose level. Insulin is secreted primarily in response to an elevated level of glucose in the blood and reacts to reduce the level of glucose in the blood. The pancreas regulates blood glucose levels through insulin secretion. Inadequate levels of insulin production, or abnormal functioning of pancreas or the endocrine cell cluster, tissues or associated ducts causes inadequate insulin production, leading to elevated blood glucose levels and thereby, causing diabetes.

In one embodiment of the present disclosure, a method for monitoring or treating a subject suffering from pancreatic disorder is provided. The method comprises monitoring nerve activity of the subject, decoding nerve signals and correlating the nerve signals to blood glucose levels and/or metabolic biomarkers. The method further comprises delivery of nerve stimulation to provide a closed loop system and to continuously monitor neural activity in real-time and thereby, provide correlation to one or more disease or disorder.

Pancreatic disorder, for example, diabetes exists in two forms: Type 1 diabetes and Type 2 diabetes. Type 1 diabetes is diagnosed in children and young adults and known as terminal diabetes. In Type 1 diabetes the body does not produce insulin. Type 1 diabetes include conditions such as, without limiting, hypoglycemia, hyperglycemia, ketoacidosis, and/or celiac disease, resulting in further complication in other organs in the body such as heart, kidneys, lungs, eyes, wound healing, etc.

Type 2 diabetes is a more common and is caused by the body's inability to produce sufficient amount of insulin or the cells ignore the insulin that is being produced by the pancreas. Type 2 diabetes may lead to damage of the eyes, kidneys and nerves and/or heart, etc. In both type 1 and type 2 diabetes, the pancreas, pancreatic tissues, cells, and associated ducts propagate nerve activity to and from the organ to the rest of the body. The nerve activity, thus propagated comprises information such as, without limiting, the state of the pancreas, and the cellular condition, insulin production, the body's ability or inability to produce insulin, and the body's ability to metabolize blood sugar and/or convert energy. This information related to, for example, the metabolic state, insulin or endocrine system and the related nervous activity is used separately or in combination with chemical, biological, medical devices and/or pharmaceutical, hormonal agents to treat disorder(s) associated with the pancreas.

In a specific embodiment, nervous activity of a subject is monitored and recorded at a portion of the vagus nerve, such as the cervical vagus nerve, hepatic vagus nerve or celiac plexus. In some embodiments, the nervous activity at the thoracic splanchnic nerve and/or the superior mesenteric plexus may be monitored and recorded. The nervous activity is further decoded and correlated to one or more diseases or disorders.

In further embodiments, the vagus nerve is stimulated to affect the operation of the pancreas to monitor and/or treat pancreas-related disease, condition or disorder. Stimulation of the portion of the vagus nerve, which is a parasympathetic nerve system, is used to modify the hyper-responsive reaction of the endocrine operation, and/or the exocrine operation of the pancreas. Additionally, embodiments of the present disclosure also include use of chemical, medical device, magnetic and/or a biological treatment to enhance the current method. Additional treatment may be performed subsequent to or in combination with the disclosed treatment methods.

In an embodiment, the invention provides a system for monitoring, decoding, and stimulating nervous activity. The system may include an electrode and a computing device. The electrode may be a bipolar cuff-type electrode configured to be implanted into a mammal's body. In embodiments, the electrode may be implanted around and/or attached to the vagus nerve, for example, at the celiac plexus. The electrode may have one or more recording electrode surfaces, and one or more stimulating electrode surfaces. The recording electrode surfaces may be configured to detect and/or record nervous activity and/or signals. The stimulating electrode surfaces may be configured to stimulate, such as by emitting an electrical pulse, nervous activity and/or signals.

In the exemplary embodiment, the electrode may have arrays of alternating recording electrode surfaces and stimulating electrode surfaces. The recording electrode surfaces and stimulating electrode surfaces may be positioned around the cuff such as to make contact with the nerve from various sides and in various positions once the electrode is implanted around and/or attached to the nerve. The recording electrode surfaces and stimulating electrode surfaces may be approximately 50 to 500 $\mu m^2$ in surface area (square, circular, rectangular or any shape). The recording and stimulating electrodes may differ in size, where the stimulating electrode may be larger so that it has sufficient surface area to deliver the electrical charge required to excite the target neural pathway. A surface coating can be applied to the electrode to further increase its surface area, and/or a mechanical or chemical process can be used to roughen the surface and achieve the same end result.

The computing device may include a processor and a memory for storing nervous activity and/or signals recorded by the recording electrode surfaces. The computing device may decode the recorded nervous activity and/or signals to detect and/or monitor physiological activity and/or disease. The computing device may also store the decoded nervous activity and/or signals in the memory. The computing device may further include a communications interface for communicating with and/or transmitting data, such as the recorded and/or decoded nervous activity and/or signals, to another computing device external to the computing device for further processing and/or storing.

In embodiments, the system may be a closed-loop system wherein the computing device decodes the recorded nervous activity and/or detects a physiological activity, and causes the stimulating electrode surfaces to stimulate the nerve, such as by emitting an electrical pulse. In such embodiments, the computing device may be a pulse generator, or may be configured to communicate with a separate pulse generator connected to the electrode to cause such pulse generator to cause the stimulating electrode surfaces to emit the pulse.

The subject matter disclosed herein may be used in combination with or subsequent to or concurrent with any pharmaceutical drug products or biologics to treat any disease or disorder. As a non-limiting example, the subject matter disclosed herein may be used in combination with an insulin pump to administer insulin depending upon the correlation of nerve activity to a biomarker or physiological parameter related to insulin levels in the human body. Another non-limiting example of drug-device combination includes administration of drugs in combination with the subject matter disclosed herein. All drug-device combination encompassing the subject matter of the present application to treat, diagnose or monitor a disease state, condition or disorder is considered to be within the scope of the present disclosure for all purposes. Drugs that can be administered in accordance with the present disclosure, include, but are not limited to, antileukotrines, immune selective anti-inflammatory drugs, steroids, nonsteroidal anti-inflammatory drugs, insulin, immune-suppressing drugs, sulfonylureas, biguanides, thiazolidinediones, alpha-glucosidase inhibitors, and biologic agents.

The subject matter disclosed herein may be configured to be synchronized with wired or wireless devices. For example, the subject matter of the present application may be synchronized with for example, a smart wire-less device to facilitate real-time monitoring of the disease state or condition, thereby provide an opportunity for the patient or the physician to respond and treat the disease state, if necessary. In one embodiment, the smart device may automatically control an insulin pump to administer insulin as necessary according to the subject matter of the present disclosure. In other embodiment, the smart device may track and record the biomarker or physiological parameter such as, for example glucose levels for further data analysis and use by the patient or treating physician. In an embodiment, the smart device may track and record the biomarker or physiological parameter and, when necessary, replace momentarily recording with electrical stimulation and attempts to modify the biomarker level or physiological parameter to desired levels.

The invention provides a method for diagnosing or treating or monitoring symptoms in a subject with diabetes based on the subject's vagus nerve activity, comprising a calibration phase and a real-time diagnostic, treatment or monitoring phase, wherein the calibration phase precedes the diagnostic, treatment or monitoring phase, and wherein the calibration phase comprises correlating a plurality of vagus nerve activity measurements from a chronically implanted electrode in the subject with a plurality of concurrent measurements of glucose levels in the blood of the subject to obtain a functional relationship between blood glucose levels and vagus nerve activity recorded from the implanted electrode in the subject; and the diagnostic, treatment or monitoring phase comprises analyzing the subject's real-time vagus nerve activity in accordance with the previously obtained functional relationship to initiate a treatment method.

The subject can have type 1 diabetes or type 2 diabetes.

The symptom being monitored can be, for example, an abnormal glucose level.

The calibration phase can comprise, for example, the following steps in sequential order:

i) signal conditioning and decomposition of a raw vagal nerve recording to obtain a conditioned and decomposed signal, ii) feature detection of the signal obtained in i) to obtain a signal with feature detection, iii) dimensionality reduction and unsupervised classification of the signal obtained in ii) to obtain a signal with dimensionality reduction and unsupervised classification, iv) neural response extraction of the signal obtained in iii) to obtain a signal with event rates, v) low-pass filtering the signal with event rates to obtain a smoothed event rate signal, and vi) lagged linear regression of the smoothed event rate signals to obtain a mapping between the neural event rate signals and the blood glucose levels.

In an embodiment, the plurality of blood glucose measurements during the calibration phase comprises blood glucose levels that fluctuate naturally in the subject. In an embodiment, the plurality of blood glucose measurements during the calibration phase comprises blood glucose levels that occur in response to administration of one or more of insulin, glucose or glucagon to the subject, or in response to stimulation of the subject's vagus nerve.

The treatment method can comprise, for example, one or more of providing instructions to the subject, administering insulin, providing glucose or glucagon to the subject, stimulating the vagus nerve of the subject, or applying acoustic energy stimulus to the subject. The method can further comprise one or more recalibration phases after the treatment phase and before a subsequent treatment phase.

The invention also provides a method for diagnosing or treating or monitoring symptoms in a subject with a cytokine-mediated disease or disorder based on the subject's vagus nerve activity, comprising a calibration phase and a real-time diagnostic, treatment or monitoring phase, wherein the calibration phase precedes the diagnostic, treatment or monitoring phase, and wherein the calibration phase comprises correlating a plurality of vagus nerve activity measurements from a chronically implanted electrode in the subject with a plurality of concurrent measurements of levels of one or more cytokines in the blood of the subject to obtain a functional relationship between blood cytokine levels and vagus nerve activity recorded from the implanted electrode in the subject; and the diagnostic, treatment or monitoring phase comprises analyzing the subject's real-time vagus nerve activity in accordance with the previously obtained functional relationship to initiate a treatment method.

The disease or disorder can be, for example, one or more of inflammation, type 1 diabetes, type 2 diabetes, obesity, trauma, hemorrhagic shock, ischemia-reperfusion injury, arthritis, immune-related diseases such as colitis, sepsis, endotoxemia, pancreatitis, inflammatory bowel disease, Crohn's Disease, rheumatoid arthritis, myasthenia gravis, multiple sclerosis, systemic lupus erythematosus, autoimmune thyroiditis (Hashimoto's thyroiditis), Graves' disease, autoimmune uveoretinitis, polymyositis, fever, pain, swelling, a host response to infection, an immune response, and a disease or disorder in which it is desirable to increase the activity or level of one or more cytokines.

The cytokine can be, for example, one or more of a chemokine, a colony stimulating factor, high-mobility group protein B1 (HMGB1), an interferon (IFN), an interleukin (e.g., any of IL-1 through IL-36), a lymphokine, macrophage migration inhibitory factor (MIF), a monokine, a transforming growth factor beta (e.g., TGF-β1, TGF-β2 and TGF-β3), and a tumor necrosis factor (e.g., TNFα or TNFβ).

The cytokine can be a pro-inflammatory cytokine, such as, for example, one or more of TNF and IL-1β. The cytokine can be an anti-inflammatory cytokine, such as, for example, one or more of interleukin-4 (IL-4), interleukin-6 (IL-6), interleukin-10 (IL-10), interleukin-11 (IL-11), interleukin-13 (IL-13) and interleukin-35 (IL-35).

The symptom being monitored can be, for example, an abnormal cytokine level.

The calibration phase can comprise, for example, the following steps in sequential order:

i) signal conditioning and decomposition of a raw vagal nerve recording to obtain a conditioned and decomposed signal, ii) feature detection of the signal obtained in i) to obtain a signal with feature detection, iii) dimensionality reduction and unsupervised classification of the signal obtained in ii) to obtain a signal with dimensionality reduction and unsupervised classification, iv) neural response extraction of the signal obtained in iii) to obtain a signal with event rates, and v) passing the signal with event rates through a decoder to obtain a mapping between nerve signals and blood cytokine levels.

In an embodiment, the plurality of blood cytokine measurements during the calibration phase comprises blood cytokine levels that fluctuate naturally in the subject. In an embodiment, the plurality of blood cytokine measurements during the calibration phase comprises blood cytokine levels that occur in response to administration of one or more of a cytokine or a cytokine antagonist or inhibitor to the subject, or in response to stimulation of the subject's vagus nerve.

The treatment method can comprise, for example, one or more of providing instructions to the subject, administering a cytokine antagonist or inhibitor to the subject, stimulating the vagus nerve of the subject, or applying acoustic energy stimulus to the subject. The method can further comprise one or more recalibration phase after the treatment phase and before a subsequent treatment phase.

In a preferred embodiment, one or more recording electrodes, and optionally one or more stimulating electrodes, are chronically implanted on the subject's vagus nerve, preferably on the subject's cervical vagus nerve and/or hepatic vagus nerve.

Preferably, the subject is a mammal; more preferably the subject is a human.

The invention also provides an implantable system for monitoring, diagnosing and/or treating a disease or disorder in a subject, wherein the system comprises one or more pairs of electrodes for recording nerve activity from the subject, an interface to capture the nerve activity, a digitizer to digitize the nerve activity, a processor for processing the digitized nerve activity, a wireless external device interface for inputting biological signals to the processor and for outputting signals from the processor, and a rechargeable or replaceable battery;

wherein the system is configured to perform a method comprising a calibration phase and a real-time diagnostic, treatment or monitoring phase, wherein the calibration phase precedes the diagnostic, treatment or monitoring phase, and wherein the calibration phase comprises correlating a plurality of nerve activity measurements from a chronically implanted electrode in a subject with a plurality of concurrent measurements of levels of one or more cytokines and/or glucose in the blood of the subject to obtain a functional relationship between blood cytokine levels and/or blood glucose levels and vagus nerve activity recorded from the implanted electrode in the subject; and the diagnostic, treatment or monitoring phase comprises analyzing the subject's real-time vagus nerve activity in accordance with the previously obtained functional relationship to initiate a treatment method.

The system can comprise one or more pairs of electrodes for stimulating a nerve in the subject. The system can be configured to record from and/or stimulate the subject's vagus nerve, in particular the subject's cervical vagus nerve or hepatic vagus nerve. The implantable electrode(s) can be, for example, one or more bipolar cuff-type electrodes.

When blood glucose levels are monitored, the calibration phase can comprise, for example, the following steps in sequential order:

i) signal conditioning and decomposition of a raw vagal nerve recording to obtain a conditioned and decomposed signal, ii) feature detection of the signal obtained in i) to obtain a signal with feature detection, iii) dimensionality reduction and unsupervised classification of the signal obtained in ii) to obtain a signal with dimensionality reduction and unsupervised classification, iv) neural response extraction of the signal obtained in iii) to obtain a signal with event rates, v) low-pass filtering the signal with event rates to obtain a smoothed event rate signal, and vi) lagged linear regression of the smoothed event rate signals to obtain a mapping between the neural event rate signals and the blood glucose levels.

When blood cytokine levels are monitored, the calibration phase can comprise, for example, the following steps in sequential order:

i) signal conditioning and decomposition of a raw vagal nerve recording to obtain a conditioned and decomposed signal, ii) feature detection of the signal obtained in i) to obtain a signal with feature detection, iii) dimensionality reduction and unsupervised classification of the signal obtained in ii) to obtain a signal with dimensionality reduction and unsupervised classification, iv) neural response extraction of the signal obtained in iii) to obtain a signal with event rates, and v) passing the signal with event rates through a decoder to obtain a mapping between nerve signals and blood cytokine levels.

Stimulating the vagus nerve of a subject for treatment has been described, for example, in U.S. Pat. Nos. 9,662,490 B2 and 8,914,114 B2, and in U.S. Patent Application Publication No. US 2018/0021580 A1, the contents of all of which are incorporated herein by reference. Applying acoustic energy stimulus to a subject for treatment has been described in U.S. Patent Application Publication No. US 2018/0021214 A1, the contents of which are incorporated herein by reference.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

The following experiments are illustrative of methods, systems and devices of the present disclosure and are not to be construed as limiting.

Experiment 1

Surgical Isolation of the cervical vagus nerve: Male BALB/C, IL-1R KO (receptor knockout) mice (strain B6.129S7-Il1r1tm1Imx/J) and TNFR1/2 double KO (strain B6.129S2-Tnfrsflatm1Imx Tnfrsflbtm1Imx/J, p55- and p75-deficient) were used between 8 and 16 weeks of age. Mice were housed under 12 h reverse day/light cycle with access to food and water ad libitum. Food was withheld for the 3-4 hours prior to nerve recording and animals continued to have access to water.

Mice were induced with general anesthesia using isoflurane at 2.5% in 100% oxygen at a flow rate of about 1 L/min for 5 minutes. Mice were then placed in the supine position and maintained at 2.0% isoflurane during surgery. The core body temperature was monitored with a rectal probe and maintained around 37 deg. C. with a heating pad and heat lamp. In order to expose the cervical vagus nerve, the neck area of the mice was shaved, cleaned with povidone iodine, and a midline cervical incision was made from the level of larynx to the sternum. The submaxillary salivary glands were exposed by blunt dissection and separated through the midline fascial plane to expose the trachea. The bundle is readily identified by the pulsation of the artery. The cervical vagus nerve was delicately separated from the artery and de-sheathed by gently removing the thin connective tissue surrounding the nerve under magnification. A ground electrode was inserted between the right salivary gland and the skin. The nerve was then placed on a two-lead commercially available bipolar sling platinum-iridium cuff electrode (Cor-Tec, Germany) that was submerged briefly in saline prior to nerve placement within the cuff. The surgical area was covered with parafilm to ensure that the nerve and surgical area does not desiccate.

Recording procedure: The electrophysiological signals for BALB/c, IL1R KO and TNFR1/2 double KO mice were digitized from the cervical vagus nerve using a Plexon data acquisition system (Omniplex, Plexon Inc., Dallas, Tex.). Isoflurane was maintained at 1.75% for BALB/c mice and 1.25% for IL1R KO and TNFR1/2 double KO throughout the recording. Thirty minutes of baseline activity was recorded followed by an intraperitoneal injection of either tumor necrosis factor (TNF) or interleukin 1β (IL-1β). Vagus nerve activity was then acquired for thirty minutes, followed by a second injection of the alternate cytokine (TNF or IL-1β). Another thirty minutes was acquired post second injection. Control animals were injected with saline following the design described above.

Figure 1B:
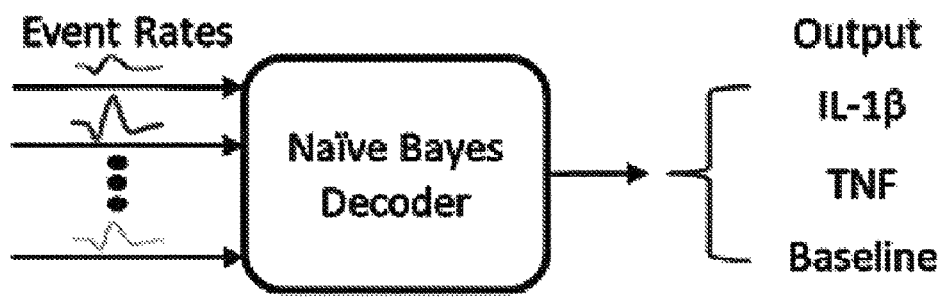
Figure 1C:
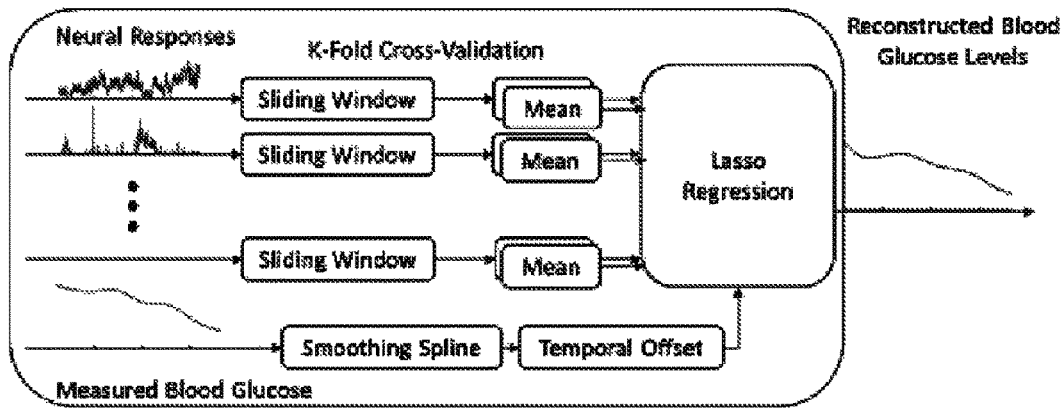
Figure 2C:
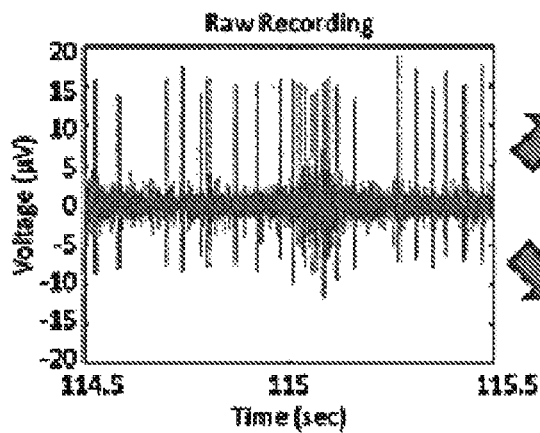
Figure 2C:
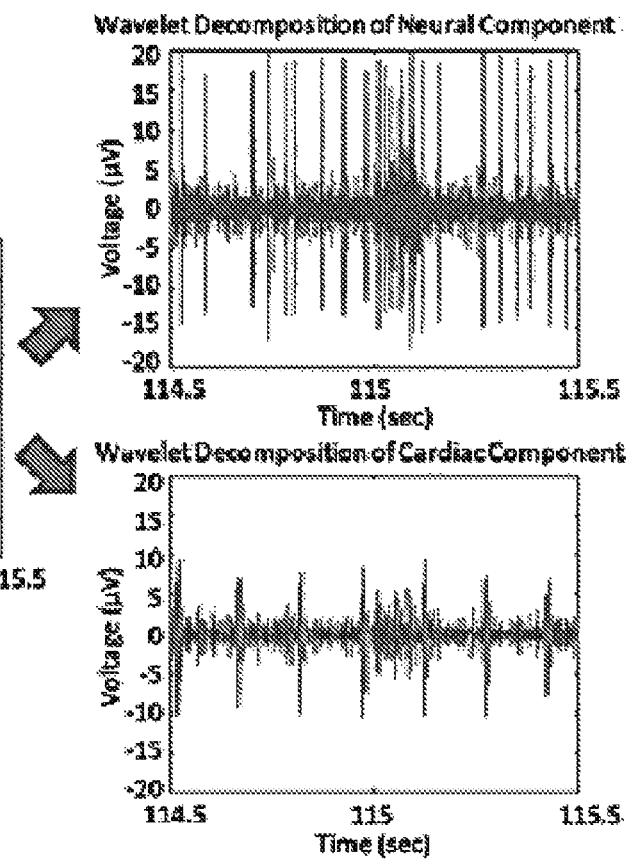
Figure 2C:
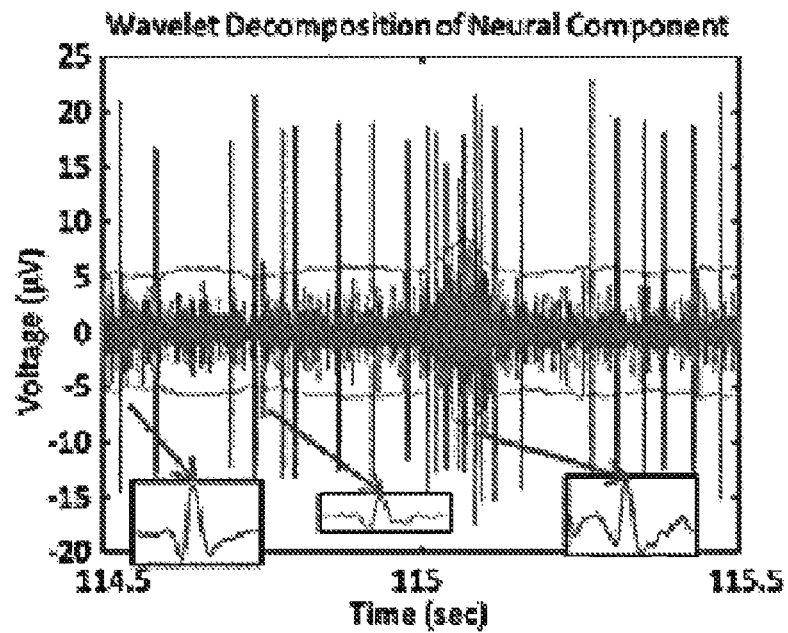
Figure 2D:
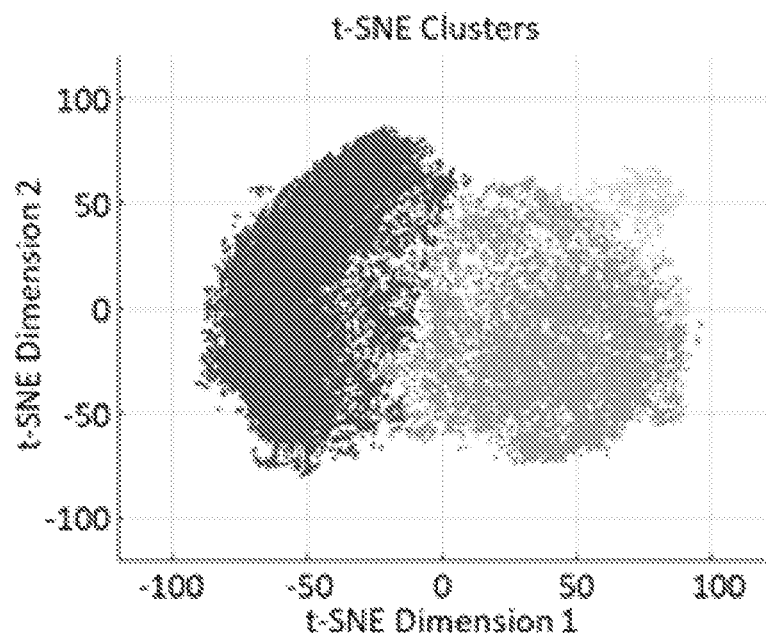
Figure 2E:
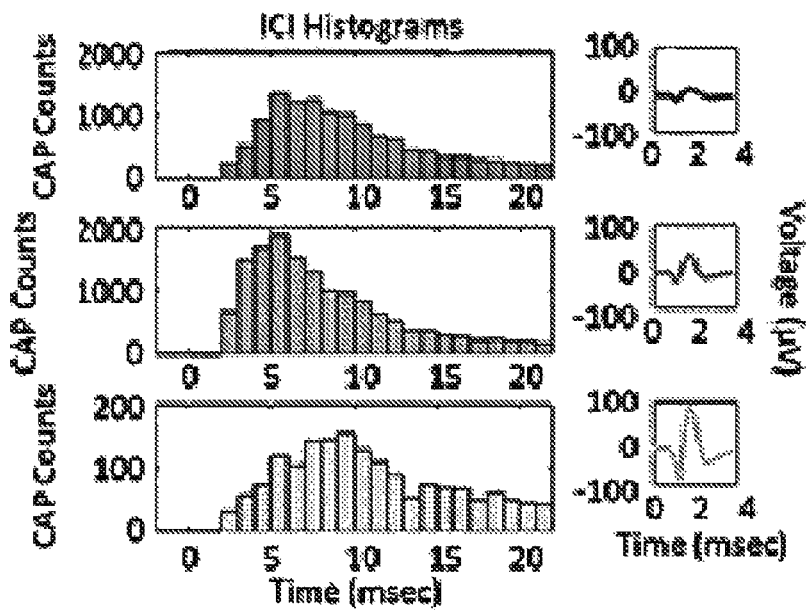

FIG. 1 is a schematic diagram of an exemplary system for recording and monitoring nerve activity, according to an embodiment of the present disclosure. FIG. 1A depicts the nerve recording processing methodological framework as a schematic diagram of the preprocessing data analysis methodological framework with all the steps carried out to extract neural responses/event rates. FIG. 1B is a schematic diagram of the decoder used to discriminate between no injection (baseline), IL-1β or TNF injection. FIG. 1C is a schematic diagram of the decoder used to regress to blood glucose levels after insulin injection.

Signal Processing: FIG. 1 depicts data analysis method and framework. Data analysis is carried out to perform among other things, cytokine discrimination. As shown in FIG. 1A, signal conditioning of the nervous activity is performed in step B. Signal conditioning removes adaptive noise present in the nerve activity. The frequency of a high order harmonic of the 60 Hz power interference was detected and tracked over time and divided by the order to adaptively estimate the fundamental frequency of the interference for use in applying a high-Q second-order IIR notch filter at each harmonic with significant power. Signal conditioning may be performed via adaptive interference removal, resampling, spectro-temporal filtering and/or artifact rejection.

Step B shown in FIG. 1A also depicts Signal Decomposition. Any method of signal decomposition may be used and is considered to be within the scope of the present disclosure. For example, wavelet decomposition (or transformation) using a Daubechies 3 type wavelet at about 1 millisecond and about 5 millisecond scales were used to enhance compound action potentials (CAPs) and cardiac artifacts respectively. Various decomposition techniques such as bandpass filtering, wavelet-based decomposition, short-time Fourier transform, and/or spectrogram estimation may be utilized for this purpose.

Step C shown in FIG. 1A depicts Feature Detection. Any method of signal detection or feature detection may be used and is considered to be within the scope of the present disclosure. For example, because the vagus nerve (VN) recording is cyclostationary consisting of the neural respiratory bursts, a smallest-of constant false alarm rate (SO-CFAR) filter was used to set an adaptive threshold that rides on the respiratory modulation. Methods such as, for example, Adaptive Compound Action Potential Thresholding, Smallest-of Constant False Alarm Rate, Spectro-temporal Feature Detection, Hilbert-based envelope methods, and/or Local Field Potential-based methods may also be utilized and are considered to be within the scope of the present disclosure.

Step D shown in FIG. 1A depicts Dimensionality Reduction & Unsupervised Classification. Any method of dimensional reduction may be used and is considered to be within the scope of the present disclosure. For example, the nonlinear dimensionality reduction technique t-Distributed Stochastic Neighbor Embedding (t-SNE) was performed to project a representative subset of the sampled CAP waveform vectors into a real two-dimensional space. Kernel t-SNE was used to map the remaining waveform vectors onto the t-SNE space. The points in the t-SNE space are organized by waveform power and waveform shape. Other methods such as, for example, Principal Component Analysis, and/or Independent Component Analysis may also be utilized. Any method of unsupervised classification may be employed and is considered to be within the scope of the present disclosure. For example, the clustering algorithm Density-Based Spatial Clustering of Applications with Noise (DBSCAN) with ε=10 and minimum Points=30 was used to perform unsupervised classification on the subset of data points used with t-SNE. K-Nearest Neighbors (KNN) with K=5 was used to perform semi-supervised classification for the waveforms mapped using kernel t-SNE. Clustering methods, such as, for example, DBSCAN, K-Means/ Davies, Gaussian Mixture Models and/or Hierarchical Clustering may also be used for this purpose.

Step E shown in FIG. 1A depicts Neural Response Extraction. Any method of neural response extraction may be used and is considered to be within the scope of the present disclosure. For example, Bin-Counting of each cluster from the unsupervised classification step by an average waveform response and a distribution of inter-CAP intervals was performed. The event rate of each CAP cluster versus time becomes a temporal sequence of features for neural decoding. Fixed Bin Counting, Stepwise Bin (Moving Average), Weighted Moving Average, and/or Kernel-based transformations (Shoenberg) may also be used and are considered to be within the scope of the present disclosure.

FIG. 1B and FIG. 1C depicts the two types of Decoding Algorithms, one for classification (FIG. 1B) and one for regression (FIG. 1C). Any method of decoding algorithm or any other algorithm may be used and is considered to be within the scope of the present disclosure. For example, without limiting, Feature Selection methods such as Regularization (Ridge, Lasso, Elastic Net), Stepwise Feature Elimination, Classification using Naïve Bayes, Support Vector Machine, Linear Discriminant Analysis, KNN, Random Forest, Regression using Lagged Linear Regression, ARMAX, Volterra Models, and/or Support Vector Regression (Radial Basis Kernels) may be used and are considered to be within the scope of the present disclosure.

In the current experiment, Principal Component Analysis (PCA) is used to project the event rates onto the directions that exhibit the most variance. K-fold cross-validation was used to minimize overfitting, and a Gaussian Naïve Bayes classifier was trained with thirty 3-fold cross-validations. The variances on the box-plots were obtained as a result of choosing 30 random folds. A confusion matrix was formed by summing the posterior probabilities of the class having the maximum posterior. This method computed the weighted percent correct classification, accounting for incorrect classifications with lower posteriors.

Results of preprocessing steps (FIG. 1A) are shown in FIG. 2. Each preprocessing step beginning from step A-E is depicted. For example, preprocessing steps starting from (A) the raw recorded signal, (B) wavelet decomposition, (C) adaptive thresholding, (D) dimensionality reduction through t-SNE and clustering using the DBSCAN method and (E) resulting CAP waveforms and Inter-CAP Interval Histograms are illustrated.

It was found that unique Compound Action Potentials may be detected and the Compound Action Potentials not only ride the respiratory modulation, but also occur at lower amplitudes, such as, between respiratory bursts.

Figure 3A:
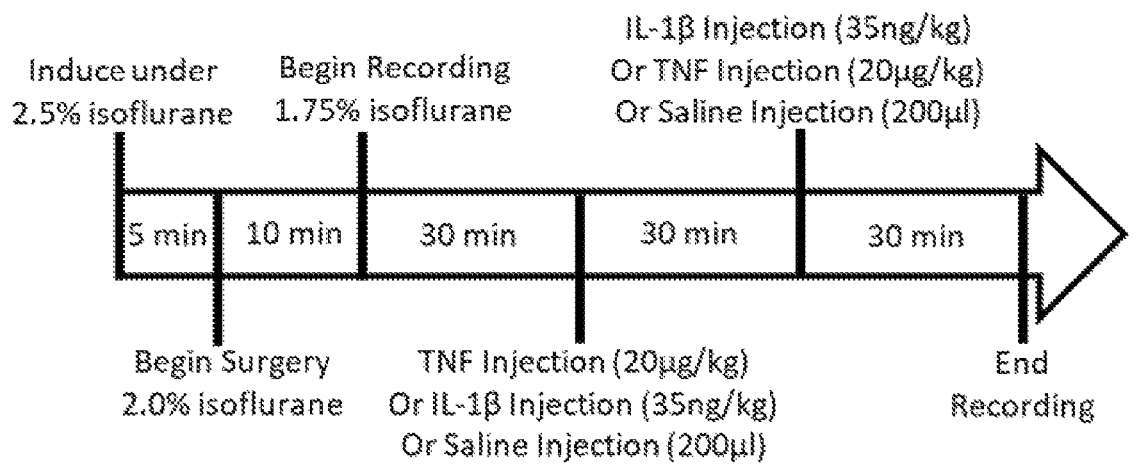
FIG. 3A-3B. Nerve recording experimental design. (A) Schematic diagram of the cytokine injection experiments. (B) Schematic diagram of the insulin/glucose injection experiments.
Figure 3B:
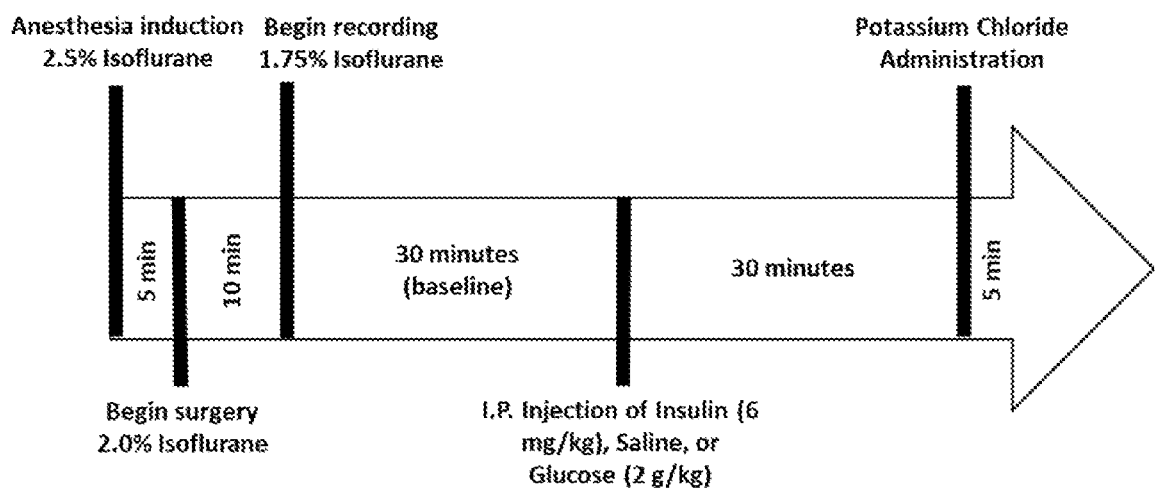

FIG. 3 outlines the nerve recording experimental design. FIG. 3A depicts a schematic diagram of the cytokine injection experiments. FIG. 3B depicts a schematic diagram of the insulin injection experiments.

Figure 4A:
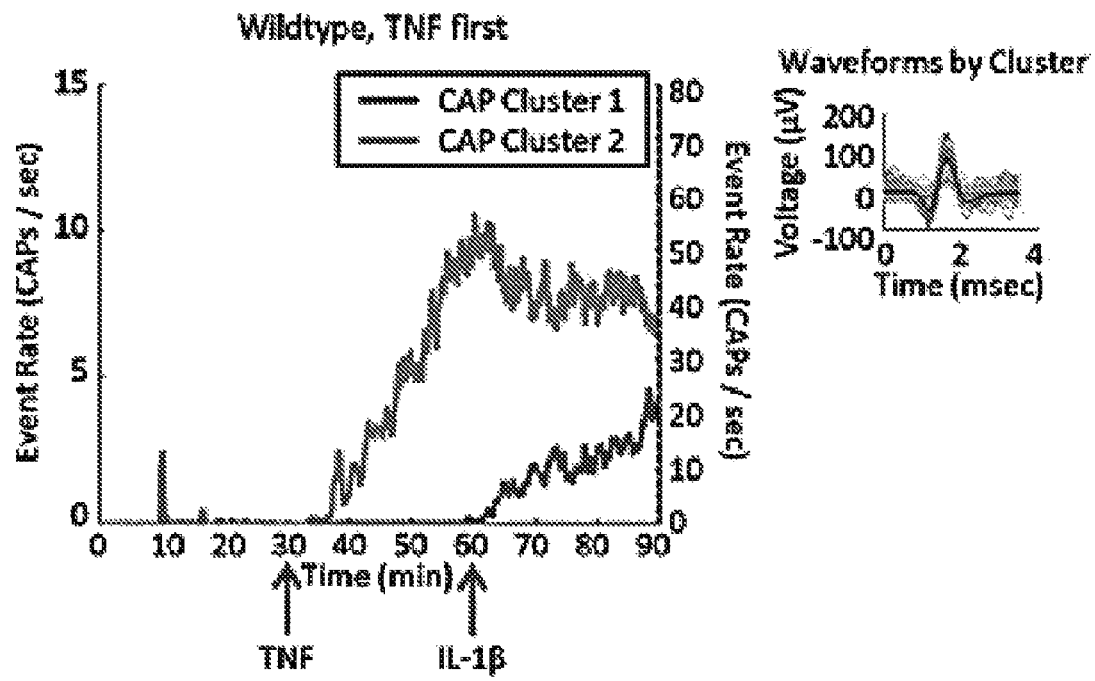
FIG. 4A-4B. Indicative examples of neural responses to different injections. To identify whether groups of neurons fire in response to TNF and IL-1β exposure, vagus nerve activity was recorded in wild type mice (n=39). Mice were defined as "responders" when at least one CAP group deviated 2 standard deviations from the peri-injection mean firing rate for at least one third of the post-injection time period. Each trace represents the response rate against time for a different CAP—solid lines correspond to lower firing rate CAPs (maximum of 15 CAPs/sec). An example of the (A) IL-1β 1st (35 ng/kg)—TNF 2nd (20 μg/kg) Vagus nerve (VN) response curve, along with their average CAP waveforms, (B) TNF 1st (20 μg/kg)—IL-1β 2nd (35 ng/kg) VN response curve, along with their average CAP waveforms. A response rate of 45% was observed in animals receiving TNF first (9 out of 20 mice) and 73.7% in the IL-1β first group (14 out of 19 mice).
Figure 4B:
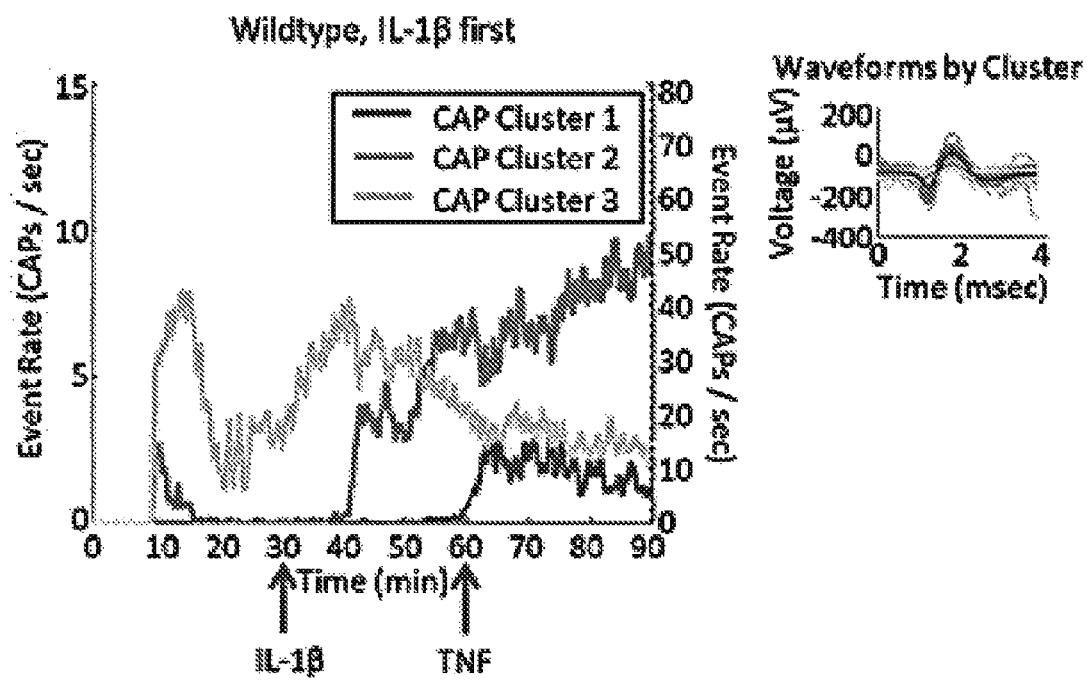

FIG. 4 shows indicative examples of neural responses to different injections. FIG. 4A shows an example of the IL-1β 1st (35 ng/kg)—TNF 2nd (20 µg/kg) VN response curve, along with their respective CAP average waveforms. FIG. 4B shows an example of the TNF $1^{st}$ (20 µg/kg)—IL-1β 2nd (35 ng/kg) VN response curve, along with their respective CAP average waveforms.

Figure 5A:
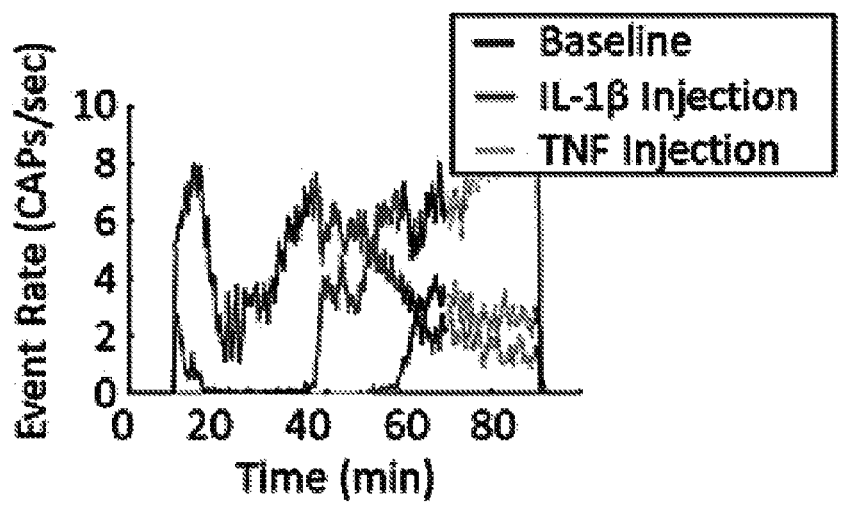
FIG. 5A-5B. Decoding Algorithm illustrative example. (A) Illustrative example of the transformation of the data from the time domain to the CAP Response domain, where the decoder detects the two responding CAP clusters. (B) Grouping the response values into the three distinct classes—baseline, IL-1β or TNF injection and using 3-fold cross validation (left panel). The concatenated out-of-sample prediction of the algorithm from all the folds to validate the algorithm (right panel) shows the result of the decoding and is indicative of its accuracy.
Figure 5B:
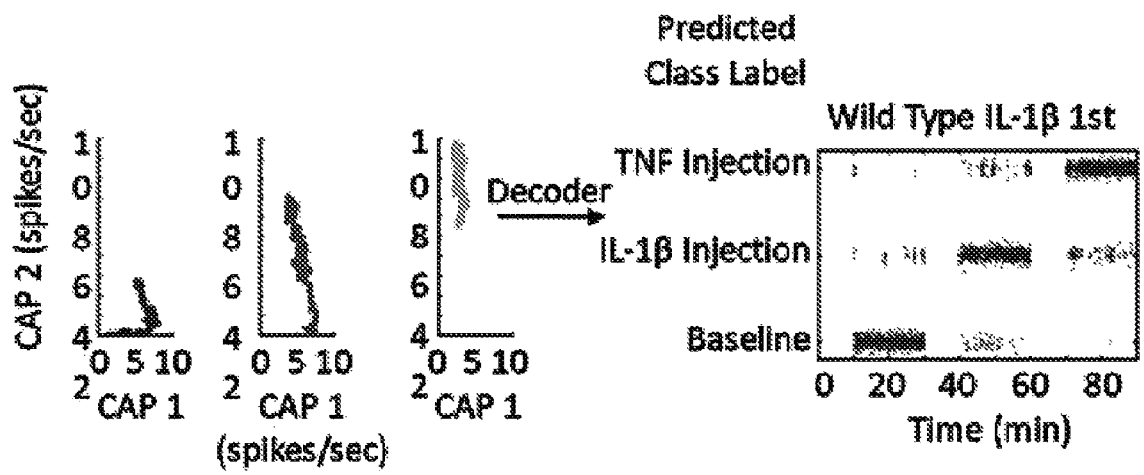

FIG. 5 depicts an illustrative example of the way the Decoding Algorithm works. FIG. 5A shows an illustrative example of the transformation of the data from the time domain to the CAP Response domain and FIG. 5B shows how the algorithm is grouping the response values into the three distinct classes—baseline, IL-1β or TNF injection using 3-fold cross validation (left panel). The concatenated out-of-sample prediction of the algorithm from all the folds to validate our algorithm (right panel) shows the result of the decoding and is indicative of its accuracy.

Figure 6A:
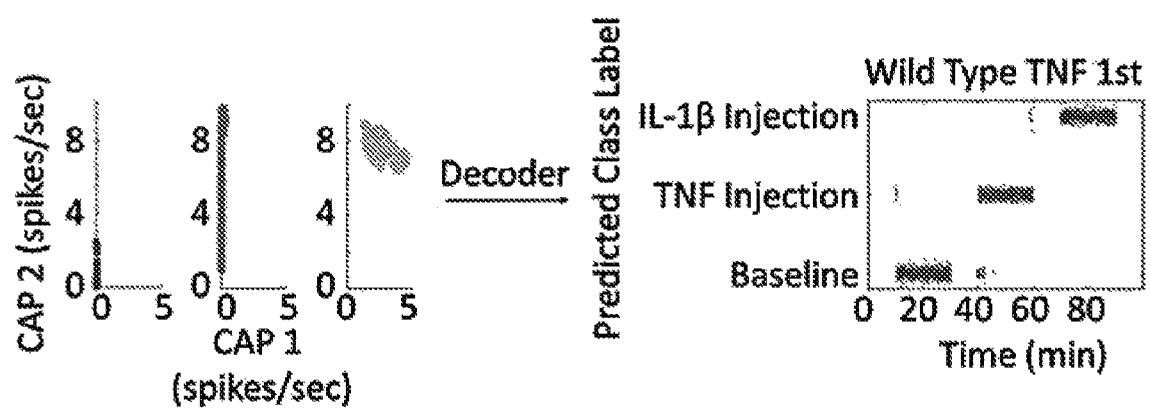
FIG. 6A-6B. Examples of decoder input and output. This decoding algorithm identified three different conditions regardless of the order of the TNF and IL-1β injections. (A) An indicative example of the TNF (20 μg/kg) 1st, IL-1β (35 ng/kg) 2nd injection experiment. The overall the success rate was 93.5±14.6% for baseline, 74.6±18.5 for TNF and 88.7±12.3 for IL-1β. An indicative example of the (B) IL-1β (35 ng/kg) 1st, TNF (20 μg/kg) 2nd injection experiments. The overall success rate was 79.6±28.6% for baseline, 91.26±11.9% for IL-1β and 69.8±21.0% for TNF. It is clear that the different injections elicit different responses and are thus successfully decoded.
Figure 6B:
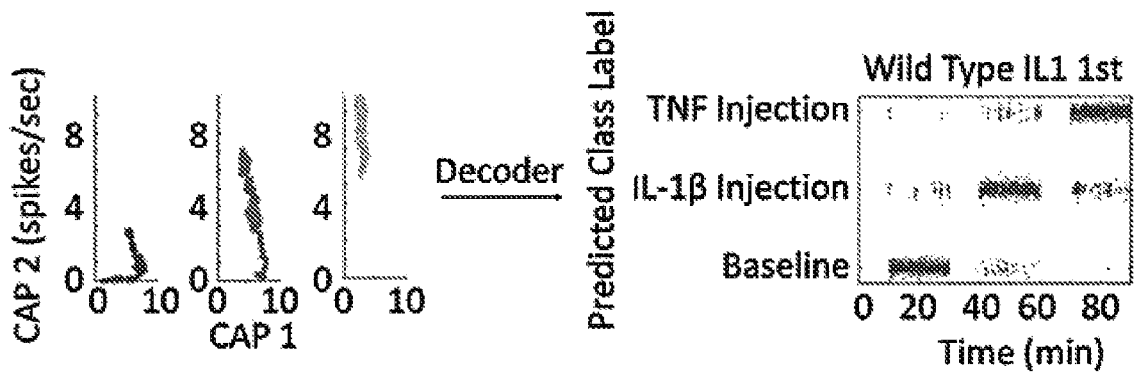

FIG. 6 shows examples of decoder input and output. This decoding algorithm identified three different conditions in either cases where TNF or IL-1β was injected first. FIG. 6A shows an indicative example of the TNF (20 µg/kg) $1^{st}$, IL-1β (35 ng/kg) $2^{nd}$ injection experiment. The overall the success rate was 93.5±14.6% for baseline, 74.6±18.5 for TNF and 88.7±12.3 for IL-1β. FIG. 6B shows an indicative example of the (B) IL-1β (35 ng/kg) $1^{st}$, TNF (20 µg/kg) $2^{nd}$ injection experiments. The overall success rate was 79.6±28.6% for baseline, 91.26±11.9% for IL-1β and 69.8±21.0% for TNF. The chance level accuracy for all decoding algorithms in this case is 33%. It is clear that the different injections elicit different responses and are thus successfully decoded.

Figure 7A:
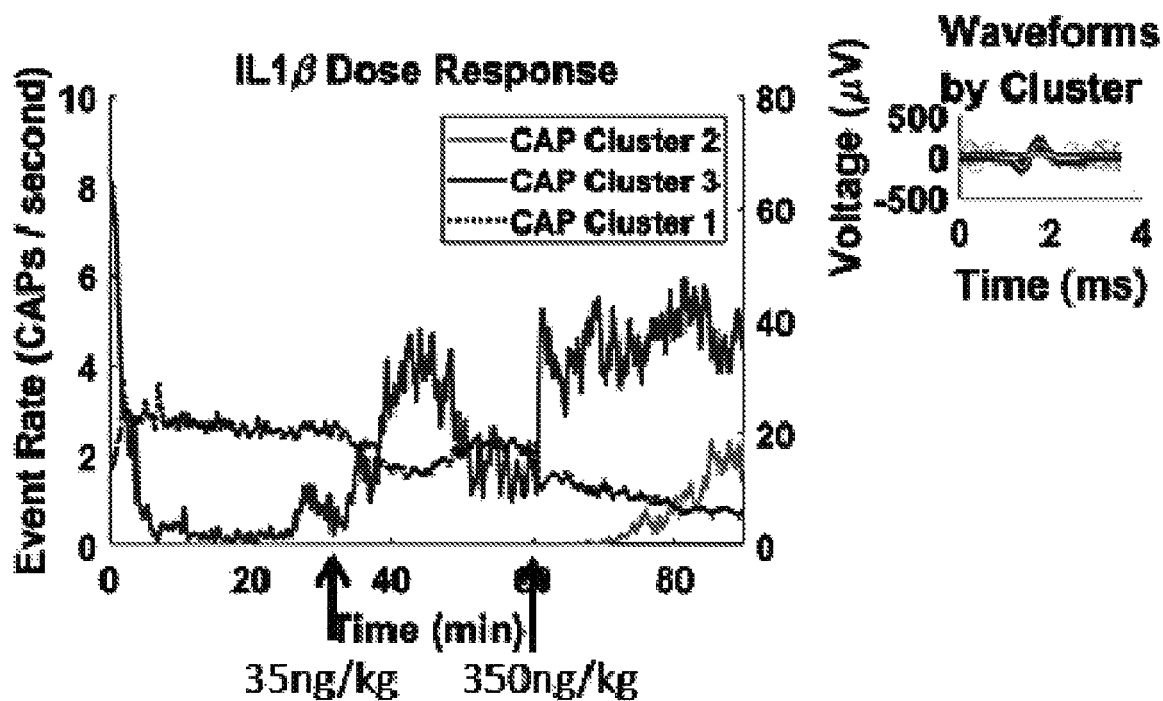
FIG. 7A-7C. Different doses of cytokines evoke different patterns. Indicative examples of neural responses to different doses of a cytokine. Each trace represents the response rate against time of a different CAP—solid lines correspond to lower firing rate CAPs (maximum of 10 CAPs/sec) and dotted lines corresponds to high firing rate CAPs (maximum of 80 CAPs/sec). (A) An example of neural responses from double dose IL-1β injections, where 35 ng/kg was injected 1st and 350 ng/kg of IL-1β 2nd, showing a clear and significant response to the both injections (left panel). Average CAP waveforms are also depicted (right panel). (B) An example of neural responses from double dose TNF injections, where 20 μg/kg was injected 1st and 200 μg/kg of TNF 2nd, showing responses to both exposures. Average CAP waveforms are also depicted (right panel). (C) Decoder output of the double dose IL-1β (upper panel) and TNF injections (lower panel), where, in both cases, the two consecutive doses are successfully decoded.
Figure 7B:
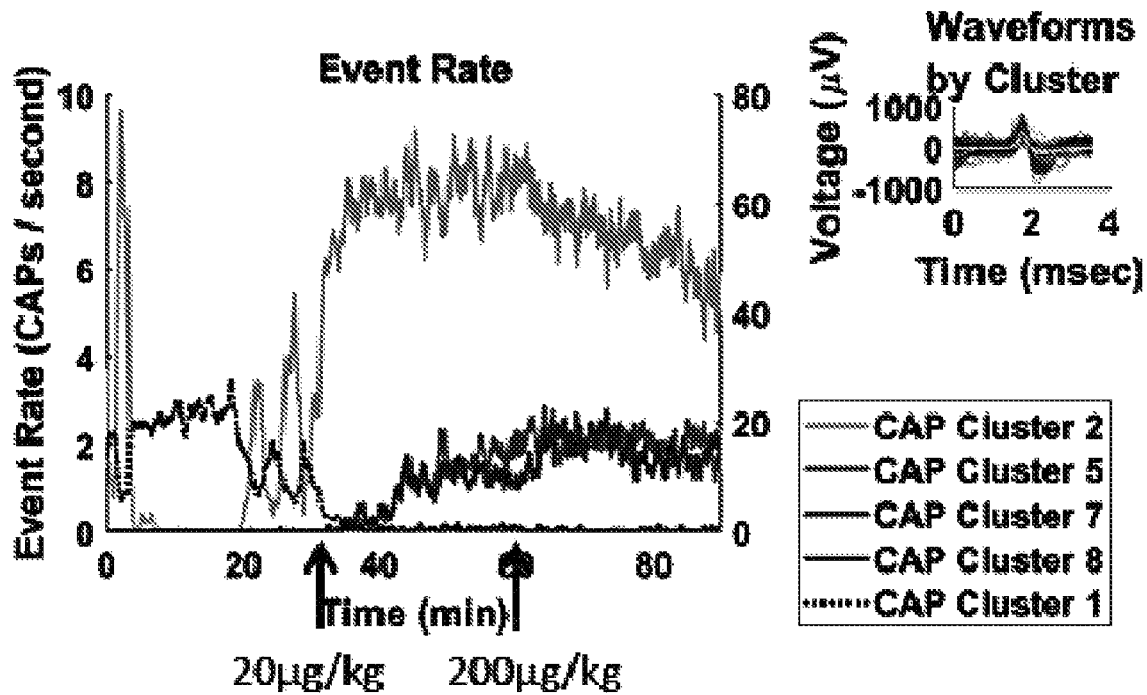
Figure 7C:
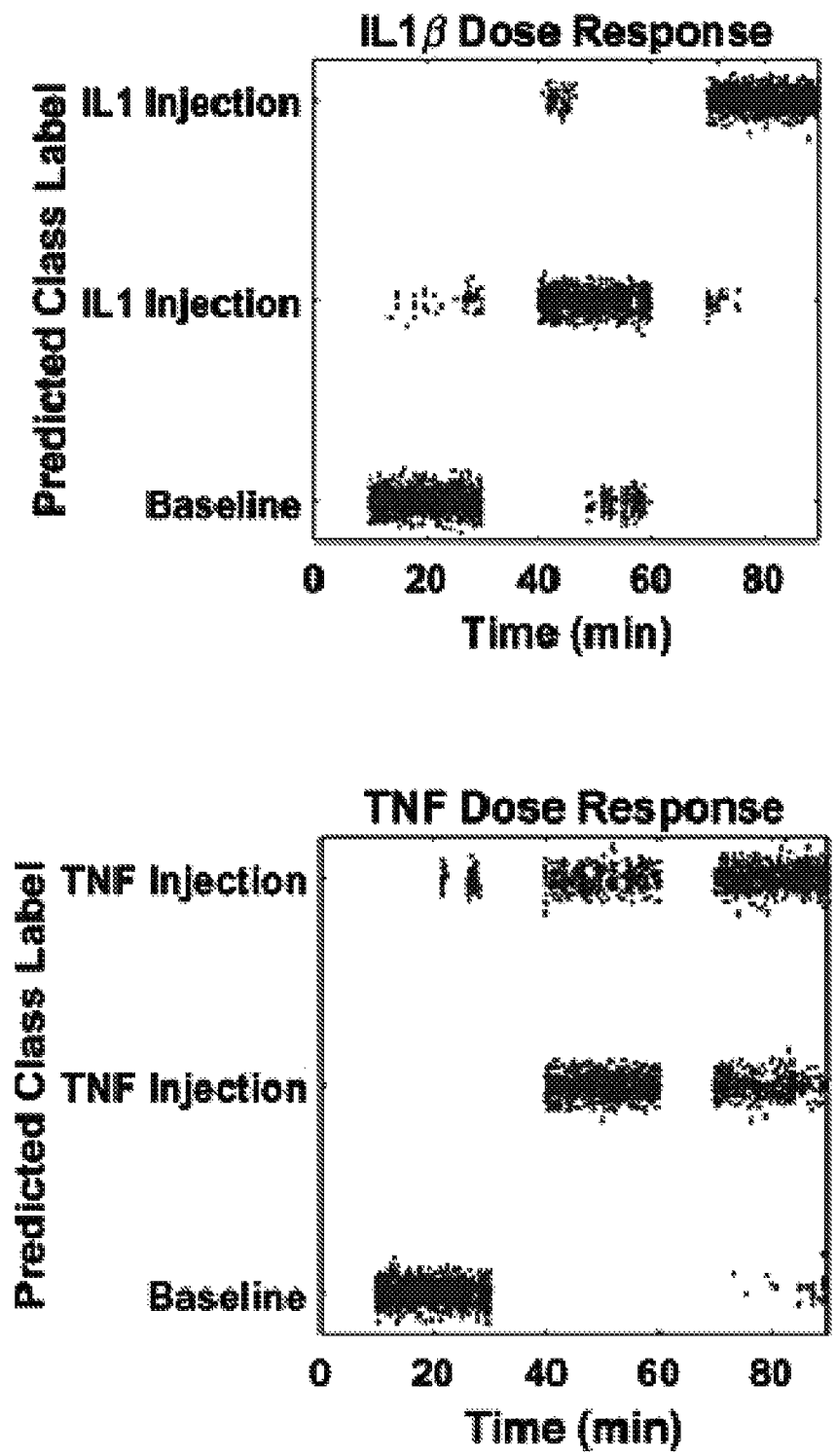

FIG. 7 outlines how different doses of cytokines evoke different patterns. Indicative examples of neural responses to different doses of a cytokine. Each trace represents the response rate against time of a different CAP—solid lines correspond to lower firing rate CAPs (maximum of 10 CAPs/sec) and dotted lines corresponds to high firing rate CAPs (maximum of 80 CAPs/sec). FIG. 7A shows an example of neural responses from double dose IL-1β injections, where 35 ng/kg were injected 1st and 350 ng/kg of IL-1β $2^{nd}$, showing a clear and significant response to the both injections. Average CAP waveforms are also depicted (right panel). FIG. 7B shows an example of neural responses from double dose TNF injections, where 20 µg/kg were injected 1st and 200 µg/kg of TNF $2^{nd}$, showing responses to both exposures. Average CAP waveforms are also depicted (right panel). FIG. 7C shows the decoder output of the double dose IL-1β (upper panel) and TNF injections (lower panel), where, in both cases, the two consecutive doses are successfully decoded.

The central nervous system also plays a critical role in maintaining energy and glucose homeostasis. The vagus nerve senses changes in systemic glucose levels and transmits the information to the central nervous system. The efferent signals generated in response are then transmitted back to the periphery to regulate glucose homeostasis.

Experiment 2: Comparative Experiment

In the current study, the goal is to leverage the information transmitted in the vagus nerve, record and decode the neural signals generated in response to metabolic changes, and use the information for devices that can monitor and control blood glucose levels in diabetic patients. Neural activity was recorded from the cervical vagus nerve of mice while simultaneously manipulating and tracking acute changes in blood glucose level. To obtain simultaneous neural recordings and glucose levels measured in the same mouse, recordings of neural event shapes and rates were analyzed and the neural data thus obtained were input into a linear regression algorithm to determine and train and correlate the data to a corresponding glucose level. Prediction algorithms were then used against actual levels of glucose measured with the glucometer, as depicted schematically in FIG. 1C.

Balb/C male mice were surgically prepared by isolating the vagus nerve on a 200 µm diameter silicone cuff electrode with bipolar leads. Mice were anesthetized with isoflurane, the nerve was fitted with electrode and activity was recorded for 1 hour using a Plexon acquisition system. Mice received 6 mg/kg insulin IP. Blood glucose dropped significantly in mice that received insulin within 10 minutes. Blood glucose was measured via tail nick with glucometer.

Figure 8:
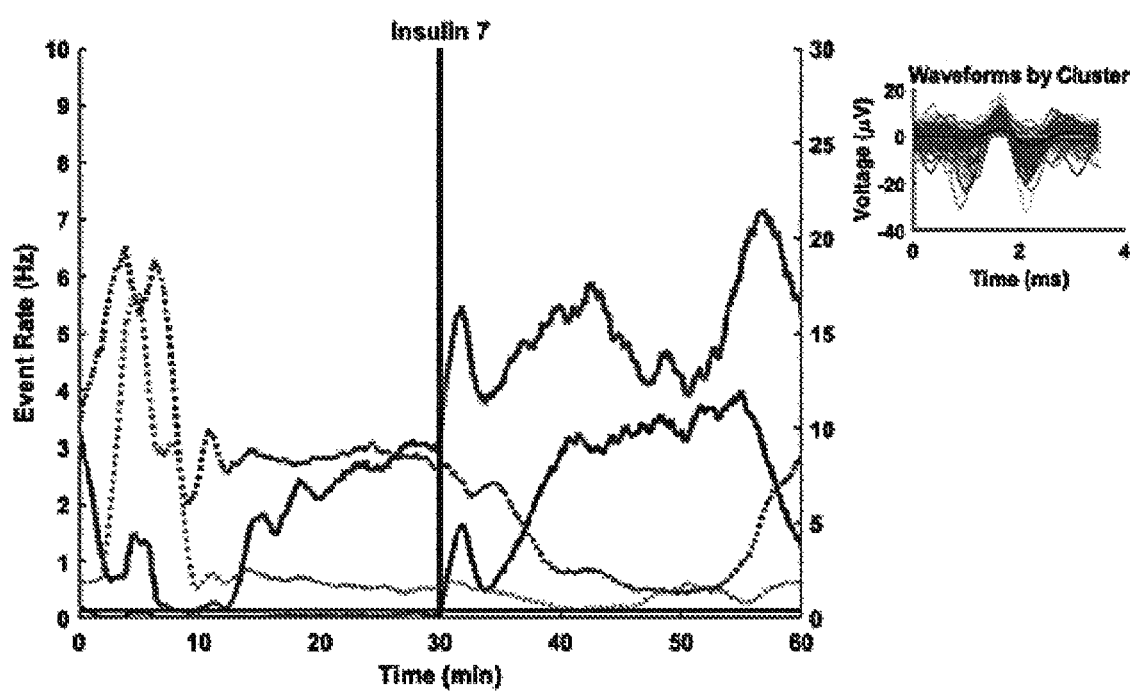
FIG. 8 plots indicative examples of neural responses to insulin injections. Indicative examples of neural responses to insulin injections. Each trace represents the response rate against time for a different CAP—solid lines correspond to lower firing rate CAPs (maximum of 10-15 CAPs/sec) and dotted lines corresponds to high firing rate CAPs (maximum of 30 CAPs/sec). The injection is indicated by a vertical black line occurring at 30 minutes. The thresholds encapsulating the baseline statistics of a particular CAP are indicated by horizontal lines. These insulin injection vagus nerve response curves include a CAP that increases its firing rate, along with their respective CAP waveforms (right panel).

FIG. 8 shows indicative examples of neural responses to insulin injections. Each trace represents the response rate against time for a different CAP—solid lines correspond to lower firing rate CAPs (maximum of 10-15 CAPs/sec) and dotted lines corresponds to high firing rate CAPs (maximum of 30 CAPs/sec). The injection is indicated by a vertical black line occurring at 30 minutes. The thresholds encapsulating the baseline statistics of a particular CAP are indicated by horizontal lines. These insulin injection VN response curves include a CAP that increases its firing rate, along with their respective CAP waveforms (right panel).

Figure 9A:
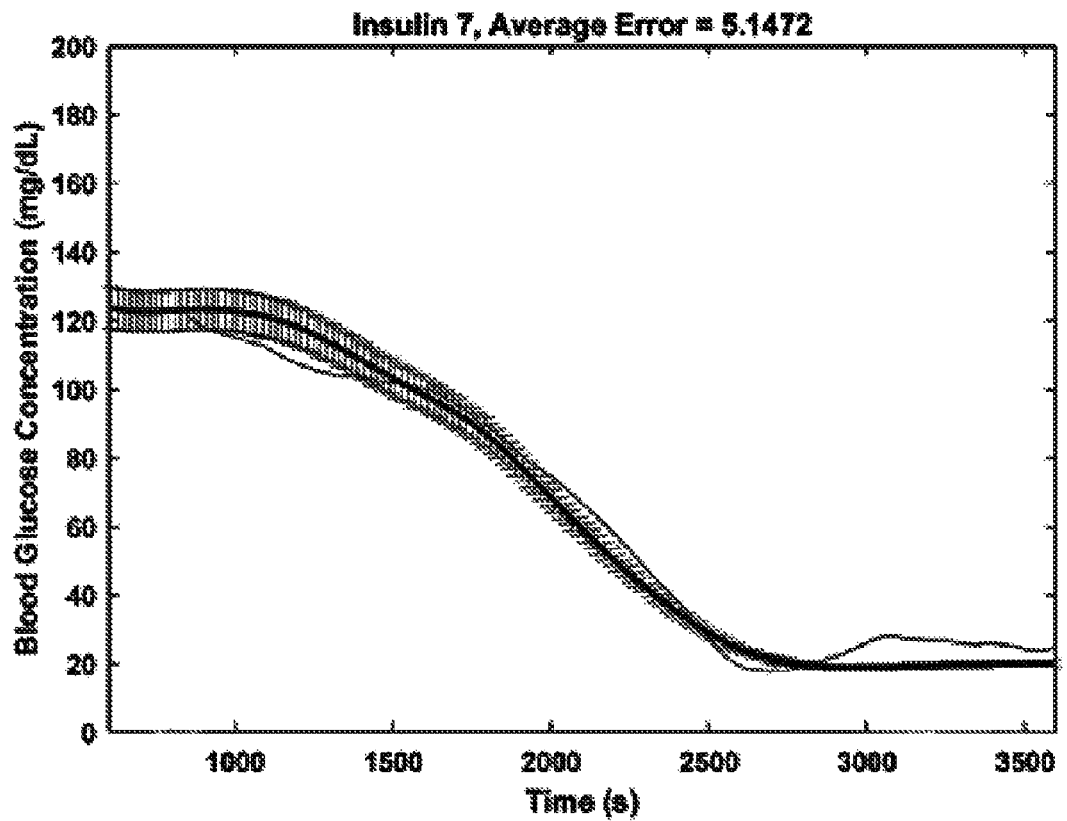
FIG. 9A-9B. (A) Indicative example of regression results of neural activity to blood glucose levels and (B) the average error across all experiments. As shown in both panels, the regression algorithm successfully reconstructs the blood glucose levels based only on the neural responses recorded from the surface of the vagus nerve.
Figure 9B:
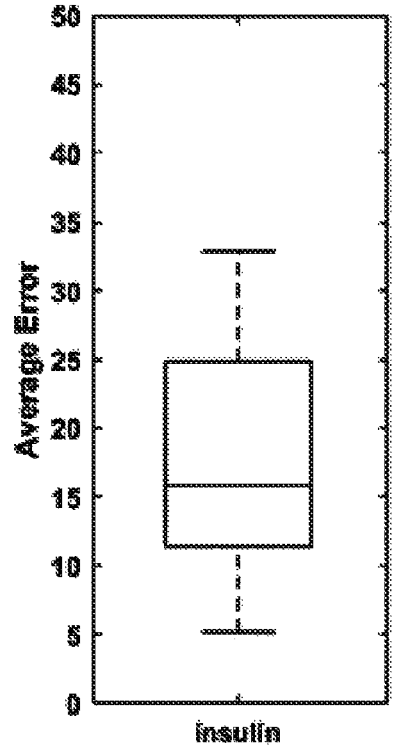

As show in FIG. 9, using multivariate, linear regression of the neural events, the algorithm can track blood glucose as it changes over time. Using only information from the neural events recorded from the vagus nerve, the glucose level of 7 different animals can be determined with a low average error, as FIG. 9B shows.

What is claimed is:

1. A method for diagnosing or treating or monitoring symptoms in a subject with diabetes based on the subject's nerve activity, wherein the nerve activity consists of vagus nerve activity, comprising a calibration phase and a real-time diagnostic, treatment or monitoring phase, wherein the calibration phase precedes the real-time diagnostic, treatment or monitoring phase, and wherein the calibration phase comprises correlating a plurality of nerve activity measurements from a chronically implanted recording electrode in the subject, wherein the nerve activity measurements consists of vagus nerve activity measurements, with a plurality of concurrent measurements of glucose levels in the blood of the subject to obtain a functional relationship between blood glucose levels and vagus nerve activity recorded from the chronically implanted recording electrode in the subject, wherein the blood glucose measurements during the calibration phase consist of one or more of blood glucose levels that fluctuate naturally in the subject and blood glucose levels that occur in response to administration of one or more of insulin, glucose and glucagon to the subject; and the real-time diagnostic, treatment or monitoring phase comprises analyzing the subject's real-time vagus nerve activity in accordance with the previously obtained functional relationship between blood glucose levels and vagus nerve activity to initiate a treatment method, wherein the treatment method consists of one or more of administering insulin, glucose or glucagon to the subject, and applying acoustic energy stimulus to the subject.

2. The method of claim 1, wherein the subject has type 1 diabetes or type 2 diabetes.

3. The method of claim 1, wherein the calibration phase comprises the following steps in sequential order:
   i) signal conditioning and decomposition of a raw vagus nerve recording to obtain a conditioned and decomposed signal,
   ii) feature detection of the signal obtained in i) to obtain a signal with feature detection,
   iii) dimensionality reduction and unsupervised classification of the signal obtained in ii) to obtain a signal with dimensionality reduction and unsupervised classification,
   iv) neural response extraction of the signal obtained in iii) to obtain a signal with event rates,
   v) low-pass filtering the signal with event rates to obtain a smoothed event rate signal, and
   vi) lagged linear regression of the smoothed event rate signals to obtain a mapping between the neural event rate signals and the blood glucose levels.

4. The method of claim 1, which further comprises a recalibration phase after the treatment phase and before a subsequent treatment phase.

5. The method of claim 1, wherein the chronically implanted recording electrode is chronically implanted on the subject's cervical vagus nerve or hepatic vagus nerve.

6. The method of claim 1, wherein the subject is a human.

7. A method for diagnosing or treating or monitoring symptoms in a subject with a cytokine-mediated disease or disorder based on the subject's vagus nerve activity, comprising a calibration phase and a real-time diagnostic, treatment or monitoring phase, wherein the calibration phase precedes the real-time diagnostic, treatment or monitoring phase, and wherein
the calibration phase comprises correlating a plurality of vagus nerve activity measurements from a chronically implanted recording electrode in the subject with a plurality of concurrent measurements of levels of one or more cytokines in the blood of the subject to obtain a functional relationship between blood cytokine levels and vagus nerve activity recorded from the chronically implanted recording electrode in the subject, wherein the blood cytokine measurements during the calibration phase consist of one or more of blood cytokine levels that fluctuate naturally in the subject and blood cytokine levels that occur in response to administration of one or more of a cytokine and a cytokine antagonist or inhibitor to the subject; and
the real-time diagnostic, treatment or monitoring phase comprises analyzing the subject's real-time vagus nerve activity in accordance with the previously obtained functional relationship between blood cytokine levels and vagus nerve activity to initiate a treatment method, wherein the treatment method consists of one or more of administering a cytokine antagonist or inhibitor to the subject and applying acoustic energy stimulus to the subject;
wherein the disease or disorder is one or more of type 1 diabetes, type 2 diabetes, obesity, trauma, hemorrhagic shock, ischemia-reperfusion injury, colitis, sepsis, pancreatitis, myasthenia gravis, multiple sclerosis, systemic lupus erythematosus, autoimmune thyroiditis (Hashimoto's thyroiditis), Graves' disease, autoimmune uveoretinitis, polymyositis, fever, and swelling.

8. The method of claim 7, wherein the one or more cytokine is one or more of a chemokine, a colony stimulating factor, high-mobility group protein B1 (HMGB1), an interferon (IFN), an interleukin (e.g., any of IL-1 through IL-36), a lymphokine, macrophage migration inhibitory factor (MIF), a monokine, a transforming growth factor beta (e.g., TGF-β1, TGF-β2 and TGF-β3), and a tumor necrosis factor (e.g., TNFα or TNFβ).

9. The method of claim 7, wherein the calibration phase comprises the following steps in sequential order:
i) signal conditioning and decomposition of a raw vagus nerve recording to obtain a conditioned and decomposed signal,
ii) feature detection of the signal obtained in i) to obtain a signal with feature detection,
iii) dimensionality reduction and unsupervised classification of the signal obtained in ii) to obtain a signal with dimensionality reduction and unsupervised classification,
iv) neural response extraction of the signal obtained in iii) to obtain a signal with event rates, and
v) passing the signal with event rates through a decoder to obtain a mapping between nerve signals and blood cytokine levels.

10. The method of claim 7, which further comprises a recalibration phase after the treatment phase and before a subsequent treatment phase.

11. The method of claim 7, wherein the chronically implanted recording electrode is chronically implanted on the subject's cervical vagus nerve or hepatic vagus nerve.

12. The method of claim 7, wherein the subject is a human.

13. An implantable system for monitoring, diagnosing and/or treating a disease or disorder in a subject, wherein the system comprises
one or more pairs of implantable electrodes for recording nerve activity from the subject, wherein the nerve activity consists of vagus nerve activity,
an implantable interface to capture the nerve activity,
an implantable digitizer to digitize the nerve activity,
an implantable processor for processing the digitized nerve activity,
an implantable rechargeable or replaceable battery; and
a wireless external device interface for inputting biological signals to the processor and for outputting signals from the processor;
wherein the system is programmed to correlate a plurality of vagus nerve activity measurements from the subject with a plurality of concurrent measurements of levels of one or more cytokines and/or glucose in the blood of the subject to obtain a functional relationship between blood cytokine levels and/or blood glucose levels and vagus nerve activity recorded from the subject; and to provide real-time diagnostic, treatment or monitoring recommendations by-analyzing the subject's real-time vagus nerve activity in accordance with the previously obtained functional relationship, and
wherein the treatment consists of one or more of administering insulin, glucose, glucagon, a cytokine antagonist or a cytokine inhibitor to the subject, and applying acoustic energy stimulus to the subject.

* * * * *